US005492919A

United States Patent [19]

Sanger et al.

[11] Patent Number: 5,492,919

[45] Date of Patent: Feb. 20, 1996

[54] 5-$HT_4$ RECEPTOR ANTAGONISTS

[75] Inventors: Gareth J. Sanger; Francis D. King; Gordon S. Baxter; Laramie M. Gaster, all of Harlow; Alberto J. Kaumann, Trumpington; Guy A. Kennett; Keith R. Mulholland, both of Harlow; Mythily Vimal, Welwyn; Kay A. Wardle; Paul A. Wyman, both of Harlow; Rodney C. Young, Oxford, all of England

[73] Assignee: SmithKline Beecham p.l.c., Brentford, Great Britain

[21] Appl. No.: 190,135

[22] PCT Filed: Jul. 31, 1992

[86] PCT No.: PCT/GB92/01419

§ 371 Date: Jul. 6, 1994

§ 102(e) Date: Jul. 6, 1994

[87] PCT Pub. No.: WO93/02677

PCT Pub. Date: Feb. 18, 1993

[30] Foreign Application Priority Data

| | | | |
|---|---|---|---|
| Aug. 3, 1991 | [GB] | United Kingdom | 9116879 |
| Oct. 23, 1991 | [GB] | United Kingdom | 9122472 |
| Jan. 23, 1992 | [GB] | United Kingdom | 9201404 |
| Apr. 4, 1992 | [GB] | United Kingdom | 9207414 |

[51] Int. Cl.$^6$ .......................... A61K 31/445; A61K 31/41

[52] U.S. Cl. .......................... 514/323; 514/364; 546/201; 548/131

[58] Field of Search .......................... 548/131; 546/201; 514/323, 364

[56] References Cited

U.S. PATENT DOCUMENTS

| | | | |
|---|---|---|---|
| 4,110,536 | 8/1978 | Havera | 544/139 |
| 4,952,587 | 8/1990 | Baker | 514/305 |
| 5,298,520 | 3/1994 | Baker | 514/383 |

FOREIGN PATENT DOCUMENTS

| | | |
|---|---|---|
| 0189002 | 7/1986 | European Pat. Off. . |
| 0200444 | 11/1986 | European Pat. Off. . |
| 0328200 | 8/1989 | European Pat. Off. . |

OTHER PUBLICATIONS

Kelarev. et al "Synthesis of amino derivatives" CA 98: 143342 (1982).

Witaker–Azmitia "The neuropharmacology of Serotonin" N.Y. Aca. Sci. 600 pp. 109–110, 195–196 (1990).

Clark. "Principles of Psychopharmacology" Academic Press, (1970) pp. 166–167.

Gotto et al "The Role of Receptors in Biology and Medicine" Raven Press, (1987) p. 191.

Steadman, C. et al., *Selective 5–Hydroxytryptamine Type 3 Receptor Antagonism With Ondansetron as Treatment for Diarrhea–Predominant Irritable Bowel Syndrome: A Pilot Study,* Mayo Clin Proc 67:732–738, 1992.

Hedge, S. et al., *Evidence for the Involvement of 5–Hydroxytryptamine 4 Receptors in 5–Hydroxytryptophan–Induced Diarrhea in Mice,* Journal Pharmacology and Experimental Therapeutics, 271:741–747, 1994.

Banner, S. et al., *5–HT Receptors and 5–Hydroxytryptophan–Evoked Defaecation in Mice,* Br. J. Pharmacol., Abstract 135P, 1993.

Journal of Medicinal Chemistry, vol. 34, No. 1, Jan 1991, American Chemical Society, C. J. Swain et al.: "Novel 5–HT3 antagonists. Indole oxadiazoles", pp. 140–151, see the entire document (cited in the application).

J Auton. Pharmacol., vol. 5, No. 2, Jun. 1985, P. R. Saxena et al.: "Excitatory 5–hydroxytryptamine receptors in the cat urinary bladder are of the M–and 5–HT2–type", pp. 101–107, see the entire document.

European Journal of Pharmacology, vol. 183, No. 4, Jul. 1990, Elsevier Science Publisher B.V., M. A. Petty et al.: "Anti arrhythmic activity of the 5–HT3 receptor antagonist MDL 73147 in different species", p. 1159, see the entire document.

Naunyn–Schmiedeberg's Arch. Pharmacol., vol. 342, No. 5, Nov. 1990, A. J. Kaumann: "Piglet sinoatrial 5–HT receptors resemble human atrial 5–HT4–like receptors", pp. 619–622, see the entire document (cited in the application).

*Primary Examiner*—Ceila Chang
*Attorney, Agent, or Firm*—Charles M. Kinzig; Stephen Venetianer; Edward T. Lentz

[57] ABSTRACT

The invention provides the use of a compound of formula (I)

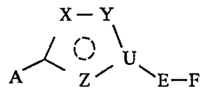

(I)

wherein A, E, F, U, X, Y, Z, are as defined in the specification, or a pharmaceutically acceptable salt thereof, for the treatment of diarrhea predominant irritable bowel syndrome.

1 Claim, No Drawings

5-$HT_4$ RECEPTOR ANTAGONISTS

This application is a 371 of PCT/GB92/01419 filed Jul. 31, 1992.

This invention relates to the use of compounds as 5-$HT_4$ receptor antagonists in the treatment of gastrointestinal disorders, CNS disorders and/or cardiovascular disorders, and to certain novel compounds having 5-$HT_4$ receptor antagonist activity.

European Journal of Pharmacology 146 (1988), 187–188, and Naunyn-Schmiedeberg's Arch. Pharmacol. (1989) 340:403–410, describe a non classical 5-hydroxytryptamine receptor, now designated the 5-$HT_4$ receptor, and that ICS 205-930, which is also a 5-$HT_3$ receptor antagonist, acts as an antagonist at this receptor.

PCT/GB91/00650 (SmithKline and French Laboratories Limited) describes the use of cardiac 5-$HT_4$ receptor antagonists in the treatment of atrial arrhythmias and stroke.

Some 5-$HT_3$ receptor antagonists have been disclosed as of potential use in the treatment of certain aspects of irritable bowel syndrome [see EP-A-189002 (Sandoz Limited) and EP-A-200444 (Beecham Group p.l.c)].

5-$HT_3$ receptor interactions which are of potential use in the treatment of IBS are those associated either with the visceral pain and abnormal perception of sensation aspects of this disease, or they are related to the ability of some 5-$HT_3$ receptor antagonists to cause constipation in volunteers.

Some 5-$HT_3$ receptor antagonists have been disclosed as of potential use in the treatment of gastrointestinal disorders associated with upper gut motility [see EP-A-226266 (Glaxo Group Ltd.) and EP-A-189002 (Sandoz Limited)]. 5-$HT_3$ receptor antagonists are also well known antiemetics, such as ondansetron, granisetron and tropisetron (see Drugs of the Future 1989, 14 (9) p.875—F. D. King and G. J. Sanger).

EP-A-328200 and U.S. Pat. No. 4952587 (Merck Sharp & Dohme Ltd.) disclose a group of heterocyclic compounds which are described as useful in the treatment of psychotic disorders (e.g. schizophrenia and mania); anxiety; alcohol or drug withdrawal; pain; gastric stasis; gastric dysfunction (such as occurs with dyspepsia, peptic ulcer, reflux oesophagitis and flatulence); migraine; nausea and vomiting and presenile and senile dementia (also known as Alzheimer's disease and senile dementia of the Alzheimer type respectively). Certain of the compounds are described as acting on 5-$HT_3$ receptors and this is attributed in whole or in part, for the pharmacological activity of these compounds. J. Med. Chem. 1991, 34, 140–51 (Swain et. al.) describes these and other compounds and their properties as 5-$HT_3$ receptor antagonists. J. Med. Chem. 1990, 33, 2715 describes a related group of 5-$HT_3$ receptor antagonists.

It has now been discovered that certain of the compounds embraced by the general formulae disclosed therein, and related compounds, have 5-$HT_4$ receptor antagonist properties, and are therefore of potential use in the treatment of IBS or atrial arrhythmias and stroke.

The compounds of the present invention also have a potential use in the treatment of CNS disorders such as anxiety and/or migraine, in the treatment of upper gut motility disorders and as antiemetics.

When used herein 'treatment' includes prophylaxis as appropriate.

The invention therefore provides the use of a compound of formula (I) or a pharmaceutically acceptable salt thereof:

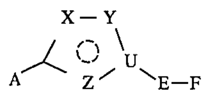

(I)

wherein the dotted circle represents one or two double bonds in any position in the 5-membered ting; X, Y and Z independently represent oxygen, sulphur, nitrogen or carbon, provided that at least one of X, Y and Z represents oxygen, sulphur or nitrogen; U represents nitrogen or carbon;

A represents a group of formula (II):

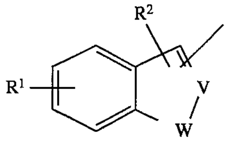

(II)

in which:

$R^1$ represents hydrogen, hydroxy, $C_{1-6}$ alkyl, $C_{2-6}$ alkenyl, $C_{2-6}$ alkynyl, $C_{1-6}$ alkoxy, hydroxy (C1-6)alkyl, halogen, amino, cyano, —$CONR^6R^7$ or —$SO_2NR^6R^7$, in which $R^6$ and $R^7$ independently represents hydrogen, $C_{1-6}$ alkyl, $C_{2-6}$ alkenyl or $C_{2-6}$ alkynyl;

$R^2$ represents hydrogen, halogen, $C_{1-6}$ alkyl, $C_{1-6}$ alkoxy or $C_{1-6}$ alkylcarbonyl;

V represents nitrogen,

—CH or —C— and

W represents oxygen, sulphur or $-NR^8$ in which $R^8$ represents hydrogen, $C_{1-6}$ alkyl, $C_{2-6}$ alkenyl or $C_{2-6}$ alkynyl;

E represents a straight or branched alkylene or alkenylene chain containing from 1 to 5 carbon atoms and optionally containing an —O—, —S—, —NH— or —Nalkyl— linkage; and F represents:

a) a non-aromatic azacyclic ring system or a non-aromatic azabicyclic ring system having carbon bridgehead(s); or.

b) a group of formula —$NR^aR^b$ wherein one of $R^a$ and $R^b$ is hydrogen or $C_{1-6}$ alkyl and the other is hydrogen, $C_{1-10}$ alkyl, $C_{2-6}$ alkenyl, $C_{2-6}$ alkynyl or aryl($C_{1-6}$)alkyl;

in the manufacture of a medicament for use as a 5-$HT_4$ receptor antagonist.

In the above formula (II):

V preferably represents N or CH;

W preferably represents $NR^8$;

$R^1$ preferably represents H; and $R^2$ preferably represents —CH—.

The group A in formula (I) is therefore preferably as indole or indazole of formula (IIA):

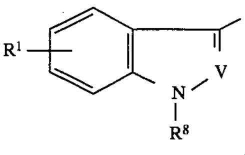

(IIA)

wherein V is N, CH or $CHR^2$ and $R^1$ are as defined for formula (I) above, and are preferably as described for formula (II) above.

The group A in formula (I) may also be replaced by a substituted phenyl moiety, as described in formula (III) of EP-A-189002, for example as described in Example 2 hereinafter.

Suitable examples of A, X, Y, Z, E and F are as described in EP-A-328200, or as in the following Examples.

Examples of alkyl or alkyl containing groups include $C_1$, $C_2$, $C_3$, $C_4$, $C_5$, $C_6$, $C_7$, $C_8$, $C_9$, $C_{10}$, $C_{11}$ or $C_{12}$ branched, straight chained or cyclic alkyl, as appropriate. $C_{1-4}$ alkyl groups include methyl, ethyl n- and iso-propyl, n-, iso-, sec- and tert-butyl. Cyclic alkyl includes cyclopropyl, cyclobutyl, cyclopentyl, cyclohexyl, cycloheptyl and cyclooctyl. Alkenyl includes all suitable values including E and Z forms.

Aryl includes phenyl and naphthyl.

Halo includes fluoro, chloro, bromo and iodo.

Suitable examples of F are as described in EP-A-328200, i.e. those having an $R^5$ substituent wherein the group E is optionally attached through $R^5$. Other examples of F of interest are those described for the compounds of the Examples hereinafter.

Suitable examples of compounds of formula (I) include that described in Example 21 of EP-A-328200, 1-methyl-3-[5-(2-(1-piperidyl)ethyl)-1,2,4-oxadiazol- 3-yl]indole. Other suitable examples of compounds of formula (I) are described in the Examples hereinafter.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

Examples of pharmaceutically acceptable salts include quaternary derivatives of the compounds of formula (I) such as the compounds quaternised by compounds $R_x$-T wherein $R_x$ is $C_{1-6}$ alkyl, phenyl-$C_{1-6}$ alkyl or $C_{5-7}$ cycloalkyl, and T is a radical corresponding to an anion of an acid. Suitable examples of $R_x$ include methyl, ethyl and n- and iso-propyl; and benzyl and phenethyl. Suitable examples oft include halide such as chloride, bromide and iodide.

Examples of pharmaceutically acceptable salts also include internal salts such as N-oxides.

The compounds of the formula (I), their pharmaceutically acceptable salts, (including quaternary derivatives and N-oxides) may also form pharmaceutically acceptable solvates, such as hydrates, which are included wherever a compound of formula (I) or a salt thereof is herein referred to.

Some of the compounds of formula (I) have at least one asymmetric centre and exist as more than one stereoisomeric form. The invention extends to each of these forms and to mixtures thereof including racemates.

The compounds of the present invention are 5-$HT_4$ receptor antagonists and it is thus believed may generally be used in the treatment or prophylaxis of gastrointestinal disorders, cardiovascular disorders and CNS disorders.

They are of potential interest in the treatment of irritable bowel syndrome (IBS), in particular the diarrhoea aspects of IBS, i.e., these compounds block the ability of 5-HT to stimulate gut motility via activation of enteric neurones. In animal models of IBS, this can be conveniently measured as a reduction of the rate of defaecation. They are also of potential use in the treatment of urinary incontinence which is often associated with IBS.

They may also be of potential use in other gastrointestinal disorders, such as those associated with upper gut motility, and as antiemetics. In particular, they are of potential use in the treatment of the nausea and gastric symptoms of gastro-oesophageal reflux disease and dyspepsia. Antiemetic activity is determined in known animal models of cytotoxic-agent/radiation induced emesis.

Specific cardiac 5-$HT_4$ receptor antagonists which prevent atrial fibrillation and other atrial arrhythmias associated with 5-HT, would also be expected to reduce occurrence of stroke (see A. J. Kaumann 1990, Naumyn-Schmiedeberg's Arch. Pharmacol. 342, 619–622, for appropriate animal test method).

It is believed that platelet-derived 5-HT induces atrial arrhythmias which encourage atrial fibrillation and atrial disorders are associated with symptomatic cerebral and sytemic embolism. Cerebral embolism is the most common cause of ischaemic stroke and the heart the most common source of embolic material. Of particular concern is the frequency of embolism associated with atrial fibrillation.

Anxiolytic activity is likely to be effected via the hippocampus (Dumuis et al 1988, Mol Pharmacol., 34, 880–887). Activity may be demonstrated in standard animal models, the social interaction test and the X-maze test.

Migraine sufferers often undergo situations of anxiety and emotional stress that precede the appearance of headache (Sachs, 1985, Migraine, Pan Books, London). It has also been observed that during and within 48 hours of a migraine attack, cyclic AMP levels are considerably increased in the cerebrospinal fluid (Welch et al., 1976, Headache 16, 160–167). It is believed that a migraine, including the prodomal phase and the associated increased levels of cyclic AMP are related to stimulation of 5-$HT_4$ receptors, and hence that administration of a 5-$HT_4$ antagonist is of potential benefit in relieving a migraine attack.

5-$HT_4$ receptor antagonist activity may be identified according to standard methods, such as those described hereinafter.

Examples of 5-$HT_4$ receptor antagonists include ICS 205-930 (tropisetron), which is described in the above mentioned patent references, R 50 595 (Janssen), which is described in FR76530 and Eur.J. Pharmacol., 181 119–125 (1990), and SDZ 205-557, which is described by K. H. Buchheit and R. Gamse in Naunyn-Schmiedeberg's Arch. Pharmacol., 343 (Suppl.), R101 (1991).

In one aspect, the compound of formula (I) is a more potent antagonist at 5-$HT_4$ receptors than at 5-$HT_3$ receptors.

Preferably, the 5-$HT_4$ receptor antagonist of formula (I) is in substantially pure pharmaceutically acceptable form.

The compounds of formula (I) may be prepared as described in EP-A-328200 and U.S. Pat. No. 4,952,587, and in the Examples and Descriptions hereinafter.

The administration of the compound may be by enteral such as oral, rectal or nasal, sublingual, transdermal or parenteral administration.

An amount effective to treat the disorder hereinbefore described depends on the usual factors such as the nature and severity of the disorder being treated and the weight of the mammal. However, a trait dose will normally contain 0.1 to 50 mg for example 0.5 to 10 mg, of the active ingredient. Unit doses will normally be administered once or more than once a day, for example 2, 3, or 4 times a day, more usually 1 to 3 times a day, such that the total daily dose is normally in the range, for a 70 kg adult of 0.1 to 50 mg, for example 0.1 to 5 mg, that is in the range of approximately 0.00 1 to 1 mg/kg/day, more usually 0.005 to 0.2 mg/kg/day.

For oral or parenteral administration, it is greatly preferred that the compound is administered in the form of a unit-dose composition, such as a unit dose oral or parenteral composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling or tabletting. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenareal edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the 5-$HT_4$ receptor antagonist and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the treatment concerned.

The present invention also provides the use of a compound of formula (I), or a pharmaceutically acceptable salt thereof in the manufacture of a medicament for use in the treatment and/or prophylaxis of irritable bowel syndrome, gastro-oesphageal reflux disease, dyspepsia, atrial arrhythmias and stroke, anxiety and/or migraine. Such treatment and/or prophylaxis may be carried out as hereinbefore described.

The present invention also provides a method of treatment and/or prophylaxis of irritable bowel syndrome, gastro-oesphageal reflux disease, dyspepsia, atrial arrhythmias and stroke, anxiety and/or migraine in mammals, including humans, which method comprises administering to the mammal in need of such treatment and/or prophylaxis, an effective and/or prophylactic amount of a compound of formula (I) or a pharmaceutically acceptable salt thereof.

The present invention further provides a pharmaceutical composition for use in the treatment and/or prophylaxis of irritable bowel syndrome, gastro-oesphageal reflux disease, dyspepsia, atrial arrhythmias and stroke, anxiety and/or migraine which comprises a compound of formula (I), or a pharmaceutically acceptable salt thereof, and a pharmaceutically acceptable carrier. Such compositions may be prepared in the manner as hereinbefore described.

The following Examples illustrate compounds for use in the invention, the following Descriptions illustrate the preparation of intermediates.

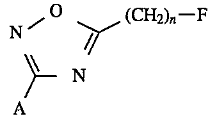

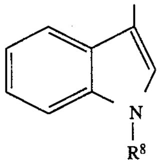 $= A^1(R^8)$ 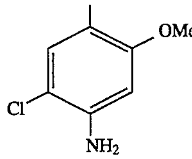 $= A^2$

| Example | A | n | F |
|---|---|---|---|
| E1 | $A^1$ | 3 | 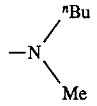 |
| E2 | $A^1$(Me) | 0 | 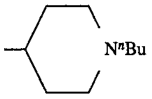 |
| E3 | $A^1$(Me) | 1 | 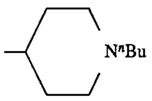 |
| E4 | $A^1$(Me) | 0 | 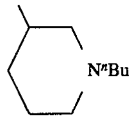 |
| E5 | $A^1$(Me) | 1 | 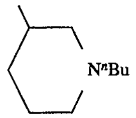 |

-continued
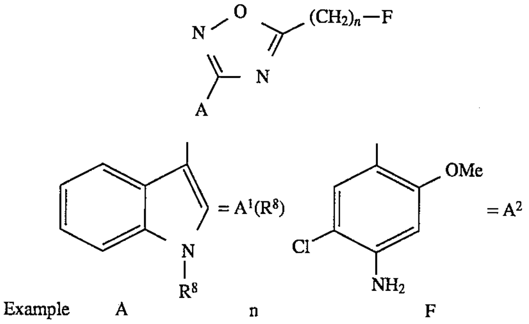
| Example | A | n | F |
|---|---|---|---|
| E6 | $A^1$(Me) | 1 | 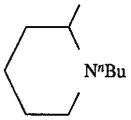 |
| E7 | $A^1$(Me) | 1 | 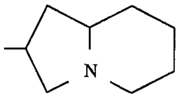 |
| E8 | $A^1$(Me) | 1 | 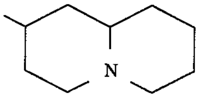 |
| E9 | $A^1$(Me) | 0 | 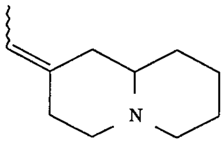 |
| E10 | $A^1$(Me) | 1 | 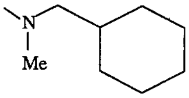 |
| E11 | $A^1$(Me) | 1 | 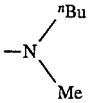 |
| E12 | $A^1$(Me) | 4 | 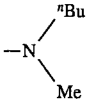 |
| E13 | $A^1$(Et) | 3 | 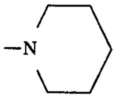 |
| E14 | $A^2$ | 3 | 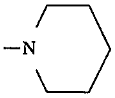 |
| E15 | $A^1$(Me) | 2 | 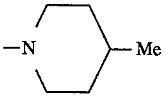 |
| E16 | $A^1$(Me) | 2 | 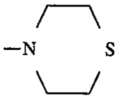 |
-continued
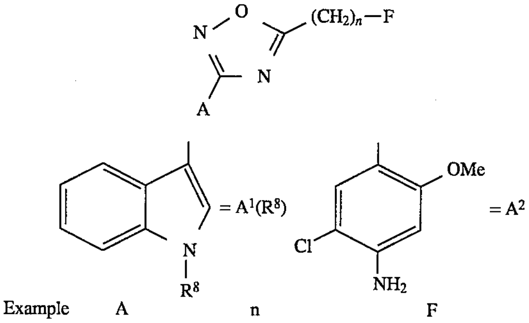
| Example | A | n | F |
|---|---|---|---|
| E17 | $A^1$(Me) | 2 | 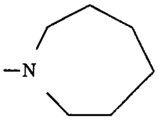 |
| E18 | $A^1$(Me) | 2 | 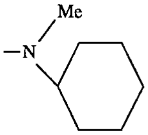 |
| E19 | $A^1$(Me) | 2 | 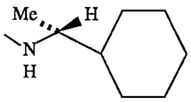 (R) |
| E20 | $A^1$(Me) | 2 | 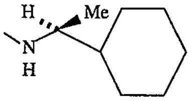 (S) |
| E21 | $A^1$(Me) | 2 | 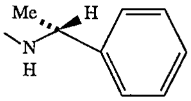 (R) |
| E22 | $A^1$(Me) | 2 | 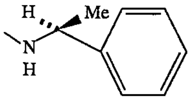 (S) |
| E23 | $A^1$(Me) | 2 | 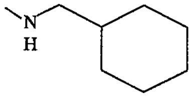 |
| E24 | $A^1$(Me) | 2 | 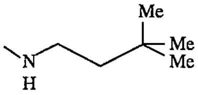 |
| E25 | $A^1$(Me) | 2 | 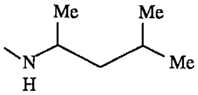 |
| E26 | $A^1$(Me) | 2 | 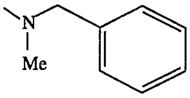 |
| E27 | $A^1$(Me) | 2 | 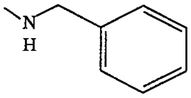 |

-continued

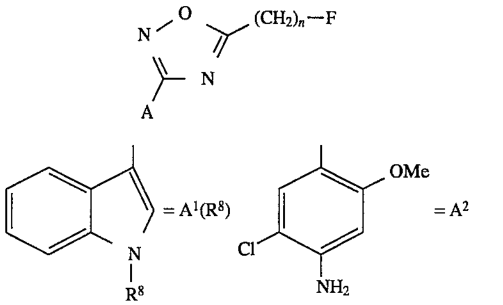

| Example | A | n | F |
| --- | --- | --- | --- |
| E28 | $A^1$(Me) | 2 | 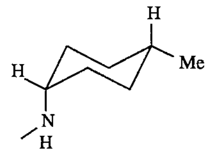 (cis) |
| E29 | $A^1$(Me) | 2 | 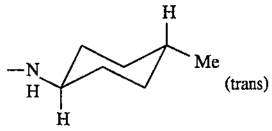 (trans) |

EXAMPLE 1

5-[3-(N-Methylbutylamino)propyl]-3-[1-methyl-1H-indol-3-yl]-1,2,4-oxadiazole (E1)

1-Methyl-1H-indole-3-carboxamide oxime (C. J. Swain et al, J.Med. Chem, 1991, 34, 147)(0.250 g, 1.33 mmol) was dissolved in dry THF (8 ml) with stirring and treated with ground 4A° molecular sieves (1 g), under nitrogen. After 30 minutes sodium hydride (80% dispersion in mineral oil) (0.044 g, 1.46 mmol) was added. The mixture was then heated to reflux, after 30 minutes, the mixture was allowed to cool momentarily, and a solution of ethyl-4-N-methylbutylaminobutyrate (0.293 g, 1.46 mmol) in dry THF (2 ml) was added. The mixture was then heated to reflux. After 6 h, the reaction mixture was allowed to cool, and was then filtered. The filter pad was then washed with THF (2×) and the filtrate evaporated under reduced pressure. The residue was then purified by silica-gel chromatography, eluting with ethyl acetate/methanol 20:1 to afford the title compound as a colourless oil (0.243 g, 56%), which was converted to its hydrochloride salt, m.pt, 174°–175° C.

$^1$H NMR (250 MHz, $CD_3SOCD_3$)

δ: 10.8 (s, 1H), 8.12 (s, 1H), 8.03 (d, J=8 Hz, 1H), 7.58 (d, J=8 Hz, 1H), 7.20–7.37 (m, 2H), 3.90 (s, 3H), 2.96–3.32 (m, 6H), 2.77 (s, 3H), 2.17–2.35 (m, 2H), 1.61–1.78 (m, 2H), 1.28–1.41 (m, 2H), 0.92 (t, J=6 Hz, 3H).

EXAMPLES 2 TO 12

The following compounds were prepared analogously:

5-[N-Butyl-4-piperidyl]-3-(1-methylindol-3-yl)-1,2,4-oxadiazole (E2)

mp 69°–70° C.

$^1$H NMR (250 MHz, $CDCl_3$) (free base)

δ: 8.24 (dd, J=8 and 1 Hz, 1H), 7.80 (s, 1H), 7.22–7.42 (m, 3H), 3.89 (s, 3H), 2.93–3.10 (m, 3H), 2.38 (t, J=8 Hz, 2H), 2.00–2.23 (m, 6H), 1.45–1.60 (m, 2H), 1.22–1.41 (m, 2H), 0.92 (t, J=6 Hz, 3H).

5N-Butyl-4-piperidylmethyl]-3-(1-methylindol-3-yl)-1,2,4-oxadiazole (E3)

mp 182°–183° C. (HCl salt)

$^1$H NMR (250 MHz, $CDCl_3$) (free base)

δ: 8.22 (dd, J=8 and 1 Hz, 1H), 7.80 (s, 1H), 7.24–7.42 (m, 3H), 3.89 (s, 3H), 2.95 (m, 2H), 2.89 (d, J=8 Hz, 2H) 2.32 (t, J=8 Hz, 2H), 1.73–2.02 (m, 5H), 1.42–1.58 (m, 2H), 1.21–1.42 (m, 2H), 0.92 (t, J=6 Hz, 3H).

5-[N-Butyl-3-piperidyl]-3-(1-methylindol-3-yl)-1,2,4-oxadiazole (E4)

mp 219°–220° C. (HCl salt)

$^1$H NMR (270 MHz, $CDCl_3$) (HCl salt)

δ: 12.80–12.98 br (s, 1H), 8.20 (dd, J=8 and 1 Hz, 1H), 7.79 (s, 1H), 7.24–7.42 (m, 3H), 4.21 (m, 1H), 3.97 (m, 1H), 3.89 (s, 3H), 3.62 (m, 1H), 2.92–3.08 (m, 2H), 2.48–2.79 (m, 3H), 1.32–1.52 (m, 2H), 1.00 (t, J=6 Hz, 3H).

5-[N-Butyl-3-piperidylmethyl]-3-(1-methylindol-3-yl]-1,2,4-oxadiazole (E5)

mp 195°–198° C. (HCl salt)

$^1$H NMR (250 MHz, $CD_3SOCD_3$)

δ: 10.80 br (s, 1H), 8.15 (s, 1H), 8.02 (d, J=8 Hz, 1H), 7.58 (d, J=8 Hz, 1H), 7.20–7.38 (m, 2H), 3.90 (s, 3H), 3.55 (m, 1H), 2.92–3.10 (m, 4H), 2.68–2.85 (m, 2H), 1.61–1.92 (m, 6H), 1.13–1.40 (m, 4H), 0.90 (t, J=6 Hz, 3H).

5-[N-Butyl-2-piperidylmethyl]-3-(1-methylindol-3-yl)-1,2,4-oxadiazole (E6)

mp 65°–68° C. (oxalate salt)

$^1$H NMR (250 MHz, $CDCl_3$) (free base)

δ: 8.21 (dd, J=8 and 1 Hz, 1H), 7.80 (s, 1H), 7.24–7.40 (m, 3H), 3.89 (s, 3H), 3.00–3.30 (m, 2H), 2.40–2.80 (m, 2H), 1.40–1.80 (m, 9H), 1.22–1.38 (m, 2H), 0.92 (t, J=6 Hz, 3H).

5-[Indolizidin-2-ylmethyl]-3(1-methylindol-3-yl)-1,2,4-oxadiazole (E7)

Higher RF isomer mp 215°–216° C. (HCl salt)

$^1$H NMR (250 MHz, $CDCl_3$) (free base)

δ: 8.22 (dd, J=8 and 1 Hz, 1H), 7.79 (s, 1H), 7.24–7.42 (m, 3H), 3.89 (s, 3H), 3.05 (m, 3H), 2.93 (dd, J=10 and 1 Hz, 1H), 2.52 (m, 1H), 2.40 (t, J=8 Hz, 1H), 2.18 (m, 1H), 1.71–2.03 (m, 5H), 1.52–1.70 (m, 1H), 1.17–1.32 (m, 3H).

Lower RF isomer mp 215°–218° C. (HCl salt)(free base)

$^1$H NMR (250 MHz, $CDCl_3$)

δ: 8.22 (dd, J=8 and 1 Hz, 1H), 7.79 (s, 1H), 7.20–7.40 (m, 3H), 3.89 (s, 3H), 3.38 (t, J=8 Hz, 1H), 3.08 (m, 1H), 2.94 (m, 2H), 2.80 (m, 1H), 1.50–2.05 (m, 9H), 1.18–1.41 (m, 2H).

5-(Quinolizidin-2-ylmethyl)-3-(1-methylindol-3-yl)-1,2,4-oxadiazole (E8)

mp 173°–175° C. (HCl salt)

$^1$H NMR (250 MHz, $CD_3SOCD_3$) (HCl salt)

δ: 10.4 (s, 1H), 8.14 (s, 1H), 8.03 (d, J=8 Hz, 1H), 7.58 (d, J=8 Hz, 1H), 7.20–7.38 (m, 2H), 3.89 (s, 3H), 3.30 (m, 1H), 2.80–3.15 (m, 5H), 2.20 (br s, 1H), 1.40–2.00 (m, 10H).

5-(Quinolizidin-2-ylmethylene)-3-(methylindol-3-yl)-1,2,4-oxadiazole (E9)

Higher RF isomer mp 226°–227° C. (HCl salt)

$^1$H NMR (250 MHz, $CD_3SOCD_3$) (HCl salt)

δ: 11.20 (br, s, 1H), 8.18 (s, 1H), 8.05 (d, J=8 Hz, 1H), 7.60 (d, J=8 Hz, 1H), 7.20–7.38 (m, 2H), 6.60 (s, 1H), 4.05 (d, J=11 Hz, 1H), 3.89 (s, 3H), 3.55 (m, 1H), 2.70–3.25 (m, 6H), 1.60–2.00 (m, 6H), 1.40–1.60 (m, 1H).

Lower RF isomer mp 227°–228° C. (HCl salt)

$^1$H NMR (250 MHz, $CD_3SOCD_3$) (HCl salt)

δ: 11.15 (br, s, 1H), 8.20 (s, 1H), 8.06 (d, J=8 Hz, 1H), 7.60 (d, J=8 Hz, 1H), 7.20–7.38 (m, 2H), 6.61 (s, 1H), 4.08 (d, J=10 Hz, 1H), 3.89 (s, 3H), 3.58 (m, 1H), 3.40 (m, 1H), 2.54–3.30 (m, 6H), 1.80–2.10 (m, 5H), 1.40–1.60 (m, 1H).

5[2-(N-Methylcyclohexylmethylamino)ethyl]-3(1-methylindol-3-yl)-1,2,4-oxadiazole (E10)

mp 162°–163° C. (HCl salt)

$^1$H NMR (250 MHz, $CDCl_3$) (free base)

δ: 8.27 (dd, J=8 and 1 Hz, 1H), 7.85 (s, 1H), 7.30–7.47 (m, 3H), 3.98 (s, 2H), 3.89 (s, 3H), 2.44 (s, 3H), 2.33 (d, J=8 Hz, 2H), 1.50–1.90 (m, 5H), 1.10–1.40 (m, 4H), 0.82–1.00 (m, 2H).

5-(N-Methylbutylaminomethyl)-3-(1-methylindol-3-yl)-1,2,4-oxadiazole (E11)

mp 182°–183° C. (HCl salt)

$^1$H NMR (250 MHz, $CDCl_3$) (free base)

δ: 8.24 (dd, J=8 and 1 Hz, 1H), 7.82 (s, 1H), 7.29–7.42 (m, 3H), 3.95 (s, 2H), 3.89 (s, 3H), 2.55 (t, J=6 Hz, 2H) 2.42 (s, 3H), 1.50–1.62 (m, 2H), 1.25–1.47 (m, 2H), 0.94 (t, J=6 Hz, 3H).

5-[4-(N-Methylbutylamino)butyl]-3-(1-methylindol-3-yl)-1,2,4-oxadiazole (E12)

mp 130°–132° C. (HCl salt)

$^1$H NMR (250 MHz, $CDCl_3$) (free base)

δ: 8.22 (dd, J=8 and 1 Hz, 1H), 7.79 (s, 1H), 7.25–7.41 (m, 3H), 3.88 (s, 3H), 2.98 (t, J=6 Hz, 2H), 2.30–2.44 (m, 4H), 2.20 (s, 3H), 1.90 (m, 2H), 1.21– 1.70 (m, 6H), 0.92 (t, J=6 Hz, 3H).

EXAMPLE 13

5-[(3-(Piperidino)propyl)]-3-(1-ethyl-1H-indol-3-yl)-1,2,4-oxadiazole (E13)

1-Ethylindole-3-ylcarboxamide oxime (200 mg, 0.98 mmol, prepared by the general method of EP-A-328200) was dissolved in anhydrous THF (4 ml) containing 4-A° powdered molecular sieves (300 mg). The mixture was stirred for 30 mins., sodium hydride (80% dispersion in oil) (40 mg, 1.3 mmol) was added and the mixture was heated at 60° C. for 20 min. It was then cooled to RT and a solution of methyl-4-piperidinyl butyrate (364 mg, 1.98 mmol) in THF (2 mol) was added. The resulting mixture was heated at reflux for 1 hr., cooled, filtered and the filtrate concentrated under vacuum. The residue was purified by column chromatography to give the product (210 mg).

mp 190°–91° C. (oxalate salt).

EXAMPLE 14

5-[3-(Piperidino)propyl]-3-(2-methoxy-4-amino-5-chlorophen-1-yl)- 1,2,4-oxadiazole. (E14)

2-Methoxy-4-amino-5-chlorobenzamide-oxime (D1)(0.250 g, 1.16 mmol) was dissolved in dry THF (8 ml) and treated with ground 4A° molecular sieves (1 g). The mixture was then stirred at room temperature for ½ h, before Nail (80% disp. in mineral oil) (0.035 g, 1.16 mmol) was added. The mixture was then heated to reflux. After ½ h the reaction mixture was allowed to cool momentarily, and methyl-4-piperidinyl-butyrate (0.242 g, 1.22 mmol)in dry THF (3 ml) was added. Reflux was then maintained for a further 4 h. The reaction mixture was then allowed to cool, and was filtered. The filter pad was washed with THF (2×), and the filtrate was evaporated under reduced pressure to give a yellow solid. The solid was purified by silica-gel chromatography using EtOAc:MeOH 98/2–95/5 as eluant to give the title compound as a white solid (0.270 g, 66%). m.pt 112°– 114° C. (from $CH_2Cl_2$/Petrol)

$^1$H NMR (270 MHz, $CDCl_3$) (free base)

δ: 7.93 (s, 1H), 6.40 (s, 1H), 4.37 (s, 2H), 3.90 (s, 3H), 2.93 (t, J=6 Hz, 2H), 2.30–2.48 (m, 6H), 1.98–2.12 (m, 2H), 1.50–1.62 (m, 4H), 1.35–1.49 (m, 2H).

EXAMPLE 15

5-[(4-Methyl-piperidino)ethyl]-3-(1-methyl-1-H-indol-3-yl)-1,2,4-oxadiazole (E15)

5-Ethenyl-3-(1-methyl-1-H-indol-3-yl)-1,2,4-oxadiazole (D2)(0.0254 g, 1.13 mmol) was dissolved in methanol (5 ml) and 4-methyl piperidine (0.167 ml, 1.69 mmol) was added. The mixture was left standing at room temperature for 16 hours, before being evaporated under reduced pressure to give a colourless oil, which was purified by silica-gel chromatography, eluting with ethyl acetate to afford the title compound as a colourless oil that crystallised on standing. The material was then converted to its hydrochloride salt, mp 192°–192° C.

$^1$H NMR (250 MHz, $CD_3SOCD_3$) (HCl salt)

δ: 10.9 br (s, 1h), 8.13 (s, 1H), 8.03 (d, J=8 Hz, 1H), 7.58 (d, J=8 Hz, 1H), 7.21–7.38 (m, 2H), 3.89 (s, 3H), 3.48–3.70 (m, 6H), 2.90–3.10 (m, 2H), 1.72– 1.90 (m, 2H), 1.43–1.70 (m, 3H), 0.90 (d, J=6 Hz, 3H).

EXAMPLES 16 TO 29

The following compounds were prepared analogously:

5-[2-(Thiomorpholino)ethyl]-3-(1-methylindol-3-yl)-1,2,4-oxadiazole (E16)

mp 121°–122° C. (free base)

$^1$H NMR (250 MHz, $CDCl_3$) (free base)

δ: 8.22 (dd, J=8 and 1 Hz, 1H), 7.80 (s, 1H), 7.27–7.42 (m, 3H), 3.89 (s, 3H), 3.13 (m, 2H), 3.00 (m, 2H), 2.85 (m, 2H), 2,69 (m, 2H).

5-[2-(Hexamethyleneimino)ethyl]-3-(1-methylindol-3-yl)-1,2,4-oxadiazole (E17)

mp 173°–175° C. (HCl salt)

$^1$H NMR (250 MHz, $CD_3SOCD_3$) (HCl salt)

δ: 11.04 br (s, 1H), 8.12 (s, 1H), 8.03 (d, J=8 Hz, 1H), 7.58 (d, J=8 Hz, 1H), 7.20–7.38 (m, 2H), 3.89 (s, 3H), 3.60 (s, 4H), 3.45 (m, 2H), 3.22 (m, 2H), 1.76–1.92 (m, 4H), 1.50–1.75 (m, 4H).

5[2-(N-Methylcyclohexylamino)ethyl]-3-(1-methylindol-3-yl)-1,2,4-oxadiazole (E18)

mp 162°–163° C. (HCl salt)

$^1$H NMR (250 MHz, $CD_3SOCD_3$) (HCl salt)

δ: 10.95 br (s, 1H), 8.22 (s, 1H), 8.04 (d, J=8 Hz, 1H), 7.59 (d, J=8 Hz, 1H), 7.20–7.38 (m, 2H), 3.79 (s, 3H), 3.40–3.80 (m, 4H), 3.22–3.40 (m, 1H), 2.80 (d, J=6 Hz, 3H), 2.10 (m, 2H), 1.82 (m, 2H), 1.08 (m, 6H).

5[2-((R)-(–)-1-Cyclohexylethylamino)ethyl]-3-(1-methylindol-3-yl)-1,2,4-oxadiazole (E19)

mp 206°–207° C. (HCl salt)

$^1$H NMR (250 MHz, $CD_3SOCD_3$) (HCl salt)

δ: 9.30 br (s, 1H), 8.88 br (s, 1H), 8.12 (s, 1H), 8.05 (d, J=8 Hz, 1H), 7.60 (d, J=8 Hz, 1H), 7.20–7.38 (m, 2H), 3.89 (s, 3H), 3.40–3.58 (m, 4H), 3.10–3.25 (m, 1H), 1.60–1.88 (m, 6H), 0.98–1.38 (m, 8H).

5[2-((S)-(+)-1-Cyclohexylethylamino)ethyl]-3(1-methylindol-3-yl)-1,2,4-oxadiazole (E20)

mp 205°–206° C.

$^1$H NMR—as given for E19

5[2-((R)-(+)-α-Methylbenzylamino)ethyl]-3-(1-methylindol-3-yl]-1,2,4-oxadiazole (E21)

mp 128°–129° C. (free base)

$^1$H NMR (250 MHz, $CDCl_3$) (free base)

δ: 8.22 (dd, J=8 and 1 Hz, 1H), 7.80 (s, 1H), 7.20–7.42 (m, 8H), 3.90 (s, 3H), 3.88 (q, J=6 Hz, 1H), 2.92–3.12 (m, 4H), 1.80 (s, 1H), 1.39 (d, J=6 Hz, 3H).

5[2-(S)-(–)-α-Methylbenzylamino)ethyl]-3-(1-methylindol-3-yl)-1,2,4-oxadiazole (E22)

mp 126°–127° C.

$^1$H NMR ($CDCl_3$)—as given for E21

5-[2-(Cyclohexylethylamino)ethyl]-3-(1-methylindol-3-yl)-1,2,4-oxadiazole (E23)

mp 204°–205° C. (HCl salt)

$^1$H NMR (250 MHz, $CD_3SOCD_3$) (HCl salt)

δ: 9.23 (s, 2H), 8.13 (s, 1H), 8.03 (d, J=8 Hz, 1H), 7.58 (d, J=8 Hz, 1H), 7.20– 7.38 (m, 2H), 3.90 (s, 3H), 3.40–3.58 (m, 4H), 2.85 (d, J=6 Hz, 2H), 1.60– 1.90 (m, 6H), 0.90–1.33 (m, 3H), 0.89–1.08 (m, 2H).

5-[2-(3,3-Dimethylbutylamino)ethyl]-3-(1-methylindol-3-yl)-1,2,4-oxadiazole (E24)

mp 215°–217° C. (HCl salt)

$^1$H NMR (250 MHz, $CD_3SOCD_3$) (HCl salt)

δ: 9.33 (s, 2H), S.13 (s, 1H), 8.04 (d, J=8 Hz, 1H), 7.58 (d, J=8 Hz, 1H), 7.20– 7.38 (m, 2H), 3.89 (s, 3H), 3.48 (m, 4H), 3.00 (m, 2H), 1.58 (m, 2H), 0.90 (s, 9H).

5-[2-(1,3-Dimethylbutylamino)ethyl]-3-(1-methylindol-3-yl)-1,2,4-oxadiazole (E25)

mp 182°–183° C. (HCl salt)

$^1$H NMR (250 MHz $CD_3SOCD_3$) (HCl salt)

δ: 9.30 (s, 2H), 8.12 (s, 1H), 8.05 (d, J=6 Hz, 1H), 7.60 (d, J=6 Hz, 1H), 7.20– 7.38 (m, 2H), 3.89 (s, 3H), 3.50 (m, 4H), 3.30 (m, 1H), 1.52–1.80 (m, 2H), 1.42 (m, 1H), 1.28 (d, J=6 Hz, 3H), 0.93 (d, J=6 Hz, 3H), 0.88 (d, J=6 Hz, 3H).

5-[2-(N-Methyl-N-benzylamino)ethyl]-3-(1-methylindol-3-yl)-1,2,4-oxadiazole (E26)

mp 156°–158° C. (HCl salt)

$^1$H NMR (250 MHz, $CD_3SOCD_3$) (HCl salt)

δ: 11.4 (s, 1H), 8.13 (s, 1H), 8.03 (d, J=8 Hz, 1H), 7.67 (m, 2H) 7.58 (d, J=8 Hz, 1H), 7.48 (m, 3H), 7.20–7.38 (m, 2H), 4.52 (m, 1H), 4.37 (dd, J15 and 5 Hz, 1H), 3.89 (s, 3H), 3.50–3.78 (m, 4H), 2.75 (d, J=5 Hz, 3H).

5-[2-(Benzylamino)ethyl]-3-(1-methylindol-3-yl)-1,2,4-oxadiazole (E27)

mp 207°–207° C. (HCl salt)

$^1$H NMR (250 MHz, $CD_3SOCD_3$) (HCl salt)

δ: 9.75 (s, 2H), 8.13 (s, 1H), 8.04 (d, J=8 Hz, 1H), 7.56–7.68 (m, 3H), 7.42– 7.52 (m, 3H), 7.20–7.38 (m, 2H), 4.26 (s, 2H), 3.40–3.55 (m, 4H).

cis-5-[2-(4-Methylcyclohexylamino)ethyl]-(1-methylindol-3-yl)-1,2,4-oxadiazole (E28)

mp 214°–216° C. (HCl salt)

$^1$H NMR (400 MHz, $CD_3SOCD_3$) (HCl salt)

δ: 9.27 br (s, 2H), 8.11 (s, 1H), 8.05 (d, J=8 Hz, 1H), 7.57 (d, J=8 Hz, 1H), 7.21–7.35 (m, 2H), 3.89 (s, 3H), 3.41–3.54 (m, 4H), 3.15–3.25 (m, 1H), 1.64– 1.85 (m, 5H), 1.43–1.54 (m, 4H), 0.92 (d, J=6 Hz, 3H).

trans-5-[2-(4-Methylcyclohexylamino)ethyl]-3-(1-methylindol-3-yl)- 1,2,4-oxadiazole (E29)

mp 206°–208° C. (HCl salt)

$^1$H NMR (400 MHz, $CD_3SOCD_3$) (HCl salt)

δ: 9.23 br (s, 2H), 8.12 (s, 1H), 8.04 (d, J=8 Hz, 1H), 7.58 (d, J=8 Hz, 1H), 7.22–7.38 (m, 3H), 3.89 (s, 3H), 3.32 (s, 4H), 2.99–3.10 (m, 1H), 2.10 (m, 2H), 1.74 (m, 1H), 1.25–1.50 (m, 3H), 0.90–1.02 (m, 4H), 0.87 (d, J=6 Hz, 3H).

EXAMPLES 30 TO 36

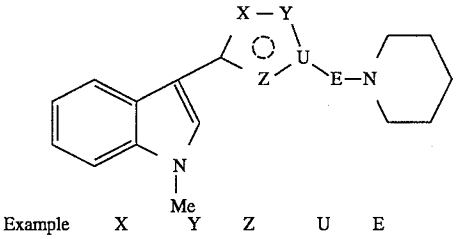

| Example | X | Y | Z | U | E |
|---|---|---|---|---|---|
| E30 | N | N | N | N | $(CH_2)_2$ |
| E31 | N | S | N | C | $S-(CH_2)_2$ |
| E32 | N | C | N | N | $(CH_2)_2$ |
| E33 | N | N | O | C | $(CH_2)_2$ |
| E34 | O | N | N | C | $(CH_2)_2$ |
| E35 | N | O | N | C | $NH-(CH_2)_2$ |

-continued

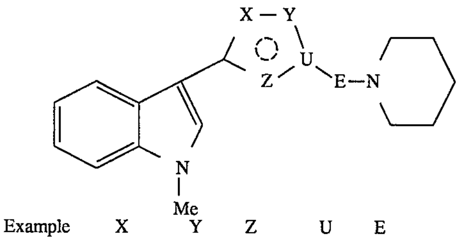

| Example | X | Y | Z | U | E |
|---|---|---|---|---|---|
| E36 | C | S | N | C | $(CH_2)_2$ |

EXAMPLE 30

3-(2-Piperidylethyl)-5-(1-methyl-1H-indol-3-yl)tetrazole (E30)

3-(1-Acetylpiperidyl)-5-(1-methyl-1H-indol-3-yl) tetrazole (0.080 g, 0.247 mmol) (D3) was dissolved in dry THF (2 ml) and added to 1M borane-tetrahydrofuran complex (0.741 ml, 0.741 mmol). The mixture was heated to reflux under $N_2$. After 1 h, a further amount of 1M borane-tetrahydrofuran complex (0.741 ml, 0.741 mmol) was added. The mixture was then heated under reflux for a further 0.5 h, before being allowed to cool. 4M HCl in methanol (1 ml) was then added and the mixture then heated under reflux for 1 h, allowed to cool, and evaporated under reduced pressure to give an oily solid which was treated with 10% NaOH. The aqueous mixture was then extracted with $CHCl_3$(2×). The combined organic layers were dried ($Na_2SO_4$) and evaporated to give the title compound as a colourless oil (0.065 g, 85%), which crystallised on standing, and was converted to its hydrochloride salt.

mp (HCl salt) 228°–230° C.

$^1$H NMR (250 MHz, $CD_3SOCD_3$) (HCl salt)

δ: 11.15 (1H,s)0.60(1H, d, J=8 Hz), 7.30(2H,m), 5.32(2H, t, J=5 Hz), 3.90(3H), s), 3.80(2H,m), 3.50(2H,m), 3.00(2H, m), 1.90–1.60(5H,m), 1.50–1.30(1H,m)

EXAMPLE 31

5(1-Thio-2-(piperidino)ethyl)-3-[1-methyl-1-H-indol-3-yl]-1,2,4-thiadiazole (E31)

5-Thio-3-[1-methyl-1H-indol-3-yl]-1,2,4-thiadiazole (0.112 g, 0.453 mmol) (D4) was dissolved in ethanol (4 ml) and sodium hydride (80%) (0.014 g, 0.475 mmol) was added with stirring: 1-(2-Chloroethyl)piperidine hydrochloride was then dissolved in ethanol (2 ml) containing sodium hydride (80%)(0.014 g, 0.475 mmol). The resultant solution was then added to the solution of the thiol. The mixture was then heated under reflux, under $N_2$. After 4 h, the reaction mixture was allowed to cool and was evaporated under reduced pressure to give an orange solid, which was partitioned between $CHCl_3$ and water. The aqueous layer was then extracted with $CHCl_3$ and the combined organic layers were dried ($Na_2SO_4$) and evaporated under reduced pressure to give a yellow oil (0.130 g). The oil was then purified by silica-gel chromatography (2:1 pentane EtOAc as eluant) to give the title compound as a colourless oil (0.110 g, 68%), which was converted to its hydrochloride salt.

mp (HCl salt) 197°–200° C.

$^1$H NMR (250 MHz, $CDCl_3$) (free base)

δ: 8.45(1H,m), 7.90(1H,s), 7.40–7.20(3H,m), 3.89(3H,s), 3.50 (2H, t, J=6 Hz), 2.82(2H, t, J=6 Hz), 2.54(4H,m), 1.65(4H,m), 1.47(2H,m).

EXAMPLE 32

1-[2-Piperidylethyl]-3(1-methyl-1H-indol-3-yl)-1,2,4-triazole hydrochloride (E32)

1-[1-Acetylpiperidyl]-3-(1-methyl-1H-indol-3-yl) 1,2,4-triazole (0.080 g, 0.248 mmol)(D5) was dissolved in dry THF (3 ml) and added to 1M borane-tetrahydrofuran complex (1.24 ml, 1.24 mmol). The mixture was then heated to reflux under $N_2$ with stirring. After 2.5 h the mixture was allowed to cool and 4M HCl in methanol was added. The reaction was then heated to reflux for 1 h before being allowed to cool, and was then evaporated under reduced pressure. The residue was then partitioned between $CHCl_3$ and 10% sodium hydroxide solution. The aqueous layer was then extracted with $CHCl_3$ and the combined organic layers were dried ($Na_2SO_4$) and evaporated under reduced pressure to give a colourless oil, which was purified by silica-gel chromatography (EtOAc:MeOH 20:1) to give the title compound as a colourless oil (0.025 g 33%), which was converted to its hydrochloride salt.

mp. 195°–197° C.

$^1$H NMR (250 MHz, $CDCl_3$) (free base)

δ: 8.34(1H, d, J=8 Hz), 8.18(1H,s), 7.73(1H,s), 7.38–7.20(3H,m), 7.38– 7.20(3H,m), 4.28(2H, t, J=6 Hz), 3.85(3H,s), 2.82(2H, t, J=6 Hz), 2.45(4H,m), 1.56–1.38(6H, m)

EXAMPLE 33

5-[2-(Piperidyl)ethyl]-3-(1-methyl-1H-indol-3-yl)-1,3,4-oxadiazole (E33)

1-[3-(1-Piperidyl)propionyl]-2-[3-carbon yl-1-methyl-1H-indol-3-yl]hydrazide (0.280 g, 0.854 mmol)(D6) was dissolved in $POCl_3$ (4 ml) and heated to reflux with stirring. After 0.75 h, the reaction mixture was allowed to cool and was poured carefully into water (15 ml). Solid sodium bicarbonate was then added to the mixture until pH 8 was reached. The resultant yellow sludge was then extracted with $CH_2Cl_2$ (3×). The combined organic layers were then dried ($Na_2SO_4$) and evaporated under reduced pressure to give a yellow oil, which was purified by silica-gel chromatography (EtOAc:MeOH 10:1 as eluant) to give the rifle compound as a colourless oil (0.148 g, 56%), which was converted to its hydrochloride salt.

mp (HCl salt) 222°–223° C.

$^1$H NMR (250 MHz, $CD_3SOCD_3$) (HCl salt)

δ: 10.82(1H,s). 8.20(1H,s), 8.10(1H, d, J=8 Hz), 7.60 (1H, d, J=8 Hz), 7.30(2H,m), 3.92(3H,s), 3.55(6H,m), 3.10–2.90(2H,m), 1.90–1.65(5H,m), 1.50–1.30(1H,m)

EXAMPLE 34

3-[2-Piperidylethyl]-5-[1-methyl-1H-indol-3-yl]-1,2,4-oxadiazole (E34)

3-(1-Piperidyl)propionamide oxime (0.903 g, 5.28 mmol)(D7) was dissolved in dry THF (40 ml) containing ground 4A molecular sieves (3.0 g). After 0.5 h sodium hydride (0.346 g, 5.76 mmol) was added and the mixture was heated to reflux under $N_2$. Meanwhile (1-methyl-1H-indol-3-yl carboxylic acid) (J. Org. Chem. 1958 23, 1096)(0.840 g, 4.80 mmol) was suspended in (CH$_2$Cl$_2$(30 ml) and oxalyl chloride was added (0.628 g, 7.20 mmol), followed by a drop of dry DMF. The mixture was then stirred at room temp. for 1.5 h, before being evaporated under reduced pressure and dried in vacuo to give the crude acid chloride, which was then dissolved in dry THF (10 ml) and added to the refluxing solution of the amidoxime salt (after 1.5 h). After 3 h the reaction mixture was allowed to cool, was filtered and the filtrate evaporated under reduced pressure to give a brown oil, which was purified by silica-gel chromatography (2% MeOH in CHCl$_3$ as eluant) to give the title compound as a colourless oil (0.546 g, 37%) which was converted to its hydrochloride salt.

mp (HCl salt ) 174°–176° C.

$^1$H NMR (250 MHz, CD$_3$SOCD$_3$) (HCl salt)

δ: 11.00(1H,s), 8.40(1H,s), 8.12(1H,d, J=8 Hz), 7.63 (1H, d, J=8 Hz), 7.40– 7.20(2H,m), 3.92(3H,s), 3.60–3.35(6H,m), 3.00(2H,m), 1.95–1.55(5H,m), 1.40(1H,m)

EXAMPLE 35

5[1-Amino-2-(piperidyl)ethyl]-3-[1-methyl-1H-indol-3-yl]-1,2,4-oxadiazole (E35)

5-Trichloromethyl-3-[1-methyl-1H-indol-3-yl]-1,2,4-oxadiazole (0.100 g, 0.316 mmol) (D8) was dissolved with stirring in 1-(2-aminoethyl) piperidine (0.8 ml) and heated to 120° C. After 0.5 h, the reaction mixture was allowed to cool and was partitioned between EtOAc and water. The organic layer was then washed with water (1×), dried (Na$_2$SO$_4$) and evaporated under reduced pressure to give a yellow oil which was purified by silica gel chromatography (10% MeOH in EtOAc as eluant) to give the title compound as a colourless oil that crystallised on standing (0.095 g, 93%).

mp 146°–147° C. from CH$_2$Cl$_2$/petrol $^1$H NMR (250 MHz, CDCl$_3$)

δ: 8.20(1H,dd, J=8 and 1 Hz), 7.70(1H,s), 7.40–7.20(3H, m), 6.10(1H,s), 3.89(3H,s), 3.54(2H,q, J=6 Hz), 2.60(2H, t, J=6 Hz), 2.45(4H,s), 1.60 (4H,m), 1.48(2H,m)

EXAMPLE 36

5-[1H-Indol-3-yl]-2-[2-piperidylethyl]-1,3-thiazole (E36)

The title compound was prepared from 3-bromoacetylindole and 1-(3-amino- 3-thioxopropyl)piperidine according to the method of Rosen T., Nagel A. A. et al, J. Med. Chem 1990, 33, 2715–2720.

mp 155°–7° C.

$^1$H NMR (250 MHz, CD$_3$SOCD$_3$ (HCl salt)

δ: 11.4 (1H,s), 8.07(1H,d), 7.87(1H,d), 7.70(1H,s), 7.43(1H,d), 7.14(2H,m), 3.55(6H,m), 2.9–3.2(2H,m), 1.7–1.95(5H,m), 1.3–1.5(1H,m)

DESCRIPTIONS

Description 1 (intermediate for Example 14)

2-Methoxy-4-amino-5 chlorobenzamide—Oxime

Sodium (0.245 g, 10.62 mmol) was dissolved in methanol (10 ml). Hydroxylamine hydrochloride (0.738 g, 10.62 mmol) in methanol (10 ml) was then added to the stirred solution. The mixture was then stirred at room temperature for ½ h, before being filtered. The filter pad was then washed with methanol (~10 ml) and the filtrate was treated with 2-methoxy- 4-amino-5-chlorobenzonitrile (A. Morimoto and Y. Saito, Jap. patent 71 03, 368, C.Abs 74, 111779h). The mixture was then heated to reflux with stirring. After 24 h, the reaction mixture was allowed to cool, and was then evaporated under reduced pressure to give a yellow solid. The solid was then recrystallised from methanol. The resulting pale yellow solid was then dried in vacuo to give the title compound (D1) (0.462 g, 40%). m.pt. 178°–181° C.

$^1$H NMR (250 MHz, (CD$_3$SOCD$_3$)

δ: 9.28 (s, 1H), 7.20 (s, 1H), 6.48 (s, 1H), 5.58 (s, 2H), 5.48 (s, 2H), 3.70 (s, 3H).

Description 2 (intermediate for Example 15)

5-Ethenyl-3-(1-methyl-1H-indol-3-yl)-1,2,4-oxadiazole

1-Methyl-1H-indole-3 carboxamide oxime (C. J. Swain et al, J Med Chem, 1991, 34, 147) (0.500 g, 2.64 mmol) was dissolved in dry THF (20 ml) with stirring, and treated with ground 4A molecular sieves (1.5 g) under nitrogen. After 30 minutes sodium hydride (80% dispersion in mineral oil) (0.087 g, 2.91 mmol) was added. The mixture was then heated to reflux. After 30 minutes the mixture was allowed to cool momentarily and a methyl acrylate (0.475 ml, 5.28 mmol) was added. The mixture was then heated to reflux for a further 3 hours. The reaction mixture was then allowed to cool and was filtered. The filter pad was then washed with THF (2×). The filtrate was then evaporated under reduced pressure. The residue was purified by silica-gel chromatography eluting with pentane EtOAc 3:1 to afford the title compound (D2) as a colourless oil that crystallised on standing rapt 53°–55° C.

$^1$H NMR (250 MHz, CDCl$_3$)

δ: 8.25 (m, 1H), 7.80 (s, 1H), 7.26–7.42 (m, 3H), 6.70–6.85 (dd, J=18, 11 Hz), 6.56 (d, J=18 Hz, 1H), 5.98 (d, J=11 Hz, 1H), 3.79 (s, 3H).

Description 3 (intermediate for Example 30)

a) 5-(1-Methyl-1H-indol-3-yl)tetrazole

3-Cyano(1-methyl-1H-indole) (J. Med. Chem. 199, 34, 147) (0.500 g, 3.21 mmol) was dissolved in dry DMF (4 ml) and treated with ammonium chloride (0.214 g, 4.01 mmol) and sodium azide (0.260 g, 4.01 mmol). The mixture was then heated to reflux with stirring. After 26 h, the reaction mixture was allowed to cool and was evaporated under reduced pressure to give a brown oil. Water (15 ml) was added to this residue whereupon it solidified. The mixture was made strongly basic with sodium hydroxide solution and then extracted with diethyl ether. The aqueous layer was then treated with activated charcoal and heated on a water bath for 10 minutes. The mixture was then filtered and the filtrate acidified with 5M HCl to pH$_4$. The resulting brown precipitate was then filtered off and dried in vacuo to give the title compound (0.125 g, 20%) as a pale brown solid.

$^1$H NMR (250 MHz, CD$_3$SOCD$_3$)

δ: 8.24(1H,dd, J=7 and 1 Hz), 8.08(1H, s), 7.60(1H, dd, J=7 and 1 Hz), 7.30(2H, m)3.91(3H,s).

b) 3-(1-Acetylpiperidyl)-5(1-methyl-1H-indol-3-yl)tetrazole 5-(1-Methyl-1H-indol-3-yl)tetrazole (0.080 g, 0.402 mmol) was dissolved in dry THF (5 ml) and treated with sodium hydride (80%) (0.014 g, 0.441 mmol). When effervescence had ceased, 1-(bromoacetyl)piperidine (Bull. Soc. Chim. France 1964 5, 1063) (0.093 g, 0.422 mmol) in dry THF (2 ml) was added. After 1 h, a further amount of 1-(bromoacetyl)piperidine (0.047 g, 0.211 mmol) in dry THF (1 ml) was added. After a further 2 h, the reaction mixture was evaporated under reduced pressure to give a brown solid which was partitioned between $CHCl_3$ and water. The organic layer was washed with $NaHCO_3$ solution, and the combined aqueous layers were extracted with $CHCl_3$. The combined organic layers were then dried ($Na_2SO_4$) and evaporated to give an off white foam which was dried in vacuo and then purified by silica-gel chromatography (pentane: EtOAc 1:1 as eluant) to give the title compound (D3) as a white solid (0.080 g, 61%)

$^1H$ NMR (250 MHz, $CDCl_3$)

δ: 8.32(1H, dd. J=7 and 1 Hz), 7.88(1H,s), 7.32(3H, m), 5.53(2H,s), 3.89(3H,s), 3.60(2H,t, J=5 Hz), 3.48(2H, t, J=8 Hz), 1.62(6H, m)

Description 4 (intermediate for Example 31)

5-Thio-3-[1-methyl(-1H-indol-3-yl]-1,2,4-thiadiazole

3-[1-Methyl(1H-indol-3-yl]carboxamide oxime (J. Med. Chem. 199, 34, 147) was dissolved in dry THF (10 ml). Ground 4A molecular sieves (1.0 g) were then added and the mixture was stirred at room temp. Sodium hydride (80%) (0.052 g, 1.746 mmol) was then added and the mixture heated to reflux for 0.5 h. Carbon disulphide (0.286 ml, 4.76 mmol) was then added. Reflux was maintained for a further 2 h, before the reaction mixture was allowed to cool. The reaction mixture was then filtered and the filtrate evaporated under reduced pressure. The resultant brown oil was then purified by silica-gel chromatography (1:1 Pentane:EtOAc as eluant) to give the title compound as a yellow solid (0.080 g, 20%)(D4)

$^1H$ NMR (250 MHz, $CD_3SOCD_3$)

δ: 8.30(1H, s), 8.20(1H,d, J=7 Hz), 7.58(1H, d, J=7 Hz), 7.28(2H,m), 3.89(3H,s).

Description 5 (intermediate for Example 32)

a) 3-(1-Methyl-1H-indol-3-yl)1,2,4-triazole

Methyl(1-methyl-1H-indol-3-yl)imidate hydrochloride (J. Chem. Soc. Perkin. Trans. 1, 1990, 3183) was dissolved with stirring in dry methanol (10 ml) and treated with trimethylamine (0.123 ml, 1.069 mmol). The reaction mixture was then stirred at room temperature for 0.25 h, then formyl hydrazide (0.064 g, 1.069 mmol) was added. The mixture was heated to reflux and after 7 h the reaction mixture was allowed to cool and was evaporated under reduced pressure. The solid residue was then dissolved in formic acid (10 ml) and refluxed for 0.75 h. The reaction mixture was allowed to cool and then evaporated under reduced pressure and purified by silica-gel chromatography (EtOAc as eluant) to give the title compound as a colourless oil (0.055 g, 31%).

$^1H$ NMR (250 MHz, $CDCl_3$)

δ: 8.20 (1H, d, J=8 Hz), 8.15(1H,s), 7.60(1H,s), 7.32–7.15(3H,m), 3.65(3H,s)

b) 1-[1-Acetylpiperidyl]-3-(1-methyl-1H-indol-3-yl)-1,2,4-triazole 3-(1-Methyl-1H-indol-3-yl)-1,2,4-triazole (0.190 g, 0.960 mmol) was dissolved with stirring in dry THF (5 ml) and was treated with sodium hydride (80%) (0.032 g, 1.05 mmol), followed by 1-(bromoacetyl)piperidine (Bull. Soc, Chim. Fr. 1964, 5, 1063–9) (0.232 g, 1.05 mmol) in dry THF (1 ml). After 4 h, the reaction mixture was evaporated under reduced pressure and partitioned between EtOAc and water. The organic layer was then dried ($Na_2SO_4$) and evaporated under reduced pressure to give a yellow oil, which was purified by silica-gel chromatography (EtOAc→ EtOAc:MeOH 100:1 as eluant) to give the title compound (D5b) as a white solid (0.080 g, 26%).

$^1H$ NMR (250 MHz, $CDCl_3$)

δ: 8.32(1H, dd, J=7 and 1 Hz), 8.21(1H,s), 7.40–7.20(3H, m), 5.06(2H, s) 3.85(3H, s), 3.62–3.48(4H,m), 1.72–1.50(6H,m).

Description 6 (intermediate for Example 33)

1-[3-(1-Piperidyl)propionyl]-2-[3-carbonyl-1-methyl(-1H-indol-3-yl] hydrazide

1-Methyl-1H-indole-3-carboxylic acid (J. Org. Chem 1958 23 1096–1097), (0.614 g, 3.51 mmol) was suspended in dry $CH_2Cl_2$ (15 ml) and treated with oxalyl chloride (0.459 ml, 5.26 mmol) with stirring, followed by a drop of DMF. After 0.75 h, the reaction mixture was evaporated under reduced pressure and dried in vacuo. The orange solid produced was then redissolved in $CH_2Cl_2$ (15 ml), triethylamine (0.512 ml, 3.86 mmol) was then added, followed by [3(1-piperidyl)propionyl]hydrazide (Seances Acad. Sci. Ser. C. (1976) 282 (17) 857–60)(0,600 g, 3.51 mmol) in $CH_2Cl_2$ (4 ml). The mixture was stirred at room temperature overnight, and washed with sodium bicarbonate solution (2×). The organic layer was dried ($Na_2SO_4$) and evaporated to give a cream solid, which was purified by silica gel chromatography (20% EtOH in $CHCl_3$ as eluant) to give the title compound (D6) (0.280 g, 24%) as a white solid.

$^1H$ NMR (250 MHz, $CDCl_3$)

δ: 9.22(1H,s), 8.10(1H,m), 7.72(1H,s), 7.30–7.10(3H,m), 3.60(3H,s), 2.70(3H,m), 2.55(4H,m), 1.75(4H,m), 1.60–1.40(2H,m)

Description 7 (intermediate for Example 34)

3(1-Piperidyl)propionamide oxime

Sodium (1.09 g, 0.047 mol) was added carefully to methanol (10 ml) under $N_2$ with stirring. When all the sodium had dissolved, a solution of hydroxylamine hydrochloride (3.29 g, 0.047 mol) in methanol (30 ml) was added slowly. The mixture was then stirred at room temp for ½ h before being filtered. The filtrate was then treated with 3(1-piperidyl)propionitrile (Chem. Abs. 47, 9906) (3.27 g, 0.024 mol) and the mixture heated to reflux. After 7.5 h the reaction mixture was allowed to cool and was then evaporated under reduced pressure. The residue was then triturated with diethylether to give a white solid which was filtered off and dried in vacuo the title compound (3.30 g, 82%) (D7)

$^1H$ NMR (250 MHz, $CD_3SOCD_3$)

δ: 9.0(1H,s), 5.60(2H,s), 3.05–2.85(6H,m), 2.42(2H, t, J=6 Hz), 1.70(4H,m), 1.50(2H,m)

Description 8 (intermediate for Example 35)

5-Trichloromethyl-3-[1-methyl-1H-indol-3-yl]-1,2,4-oxadiazole

1-Methyl-1H-indole-3-carboxamide oxime (J. Med. Chem. 1991 34, 147) (2.00 g, 0.011 mol) was added to trichloroacetic anydride (20 ml) with ice cooling and stirring. The mixture was then stirred at room temperature. After 2.5 h, the reaction mixture was poured onto a mixture of ethyl acetate and aqueous sodium bicarbonate. The aqueous layer was then extracted with ethyl acetate and the combined organic layers were dried ($Na_2SO_4$) and evaporated under reduced pressure to give a yellow solid which was purified by silica-gel chromatography (Pentane: EtOAc 10:1) to give the title compound as a cream coloured solid (1.29 g, 39%).

$^1H$ NMR (400 MHz,$CDCl_3$)

δ: 8.20(1H,dd, J=8 and 1 Hz), 7.88(1H,s), 7.40–7.20(3H, m), 3.89(3H,s)

5-$HT_4$ RECEPTOR ANTAGONIST ACTIVITY

1) Guinea pig colon

Male guinea-pigs, weighing 250–400 g are used. Longitudinal muscle-myenteric plexus preparations, approximately 3 cm long, are obtained from the distal colon region. These are suspended under a 0.5 g load in isolated tissue baths containing Krebs solution bubbled with 5% $CO_2$ in $O_2$ and maintained at 37° C. In all experiments, the Krebs solution also contains methiothepin $10^{-7}$M and granisetron $10^{-6}$M to block effects at 5-$HT_1$, 5-$HT_2$ and 5-$HT_3$ receptors.

After construction of a simple concentration-response curve with 5-HT, using 30s contact times and a 15rain dosing cycle, a concentration of 5-HT is selected so as to obtain a contraction of the muscle approximately 40– 70% maximum($10^{-9}$M approx). The tissue is then alternately dosed every 15 min with this concentration of 5-HT and then with an approximately equi-effective concentration of the nicotine receptor stimulant, dimethylphenylpiperazinium (DMPP). After obtaining consistent responses to both 5-HT and DMPP, increasing concentrations of a putative 5-$HT_4$ receptor antagonist are then added to the bathing solution. The effects of this compound are then determined as a percentage reduction of the contractions evoked by 5-HT or by DMPP. From this data, $pIC_{50}$ values are determined, being defined as the –log concentration of antagonist which reduces the contraction by 50%. A compound which reduces the response to 5-HT but not to DMPP is believed to act as a 5-$HT_4$ receptor antagonist.

The compound of Example 21 of EP-A-328200 had a $pIC_{50}$ of 7.3.

Compounds were generally active in the range of concentrations of the order of $pIC_{50}$=6 or more, E1 and E3 showing particularly good activity.

2) Piglet Atria

Compounds were tested in the piglet spontaneous beating screen (Naunyn-Schmiedeberg's Arch. Pharmacol 342, 619–622). $pK_B$ ($-\log_{10} K_B$) value for the compound of Example 21 of EP-A-328200 was 7.6.

3) Rat oesophagus

Rat oesophageal tunica muscularis mucosae is set up according to Baxter et. al. Naunyn-Schmiedeberg's Arch. Pharmacol., 343, 439–446 (1991). The inner smooth muscle tube of the muscularis mucosae is isolated and mounted for isometric tension recording in oxygenated (95% $O_2$/5% $CO_2$) Tyrodes solution at 37° C. All experiments are performed in pargyline pretreated preparations (100 μM for 15 rain followed by washout) and in the presence of cocaine (30 μM). Relaxant responses to 5-HT are obtained after precontracting the oesophagus tissue with carbachol (3μM).

4) 5-HT-induced motility in dog gastric pouch

Compounds are tested for inhibition in the in vivo method described in "Stimulation of canine motility by BRL 24924, a new gastric prokinetic agent", Bermudez et al, J. Gastrointestinal Motility, 2(4), 281–286.

We claim:

1. A method of treating diarrhea predominant irritable bowel syndrome, which comprises administering a compound selected from:

5-[3-(N-methylbutylamino)propyl]-3-[1-methyl-1H-indol-3-yl]-1,2,4-oxadiazole,

5[N-butyl-4-piperidylmethyl]-3-(1-methylindol-3-yl)-1,2,4-oxadiazole, and

5[2-((R)-(+)-α-methylbenzylamino)ethyl]-3-(1-methylindol-3-yl]-1,2,4-oxadiazole.

* * * * *